United States Patent [19]
McMahon

[11] 3,975,711
[45] Aug. 17, 1976

[54] REAL TIME FINGERPRINT RECORDING TERMINAL

[75] Inventor: Donald H. McMahon, Carlisle, Mass.

[73] Assignee: Sperry Rand Corporation, New York, N.Y.

[22] Filed: Aug. 30, 1974

[21] Appl. No.: 502,117

[52] U.S. Cl. .......................... 340/146.3 E; 250/550; 350/286; 356/71
[51] Int. Cl.² ......................................... G06K 9/00
[58] Field of Search ................ 340/146.3 E; 356/71; 350/112, 286, 287; 250/550

[56] References Cited
UNITED STATES PATENTS

| | | | |
|---|---|---|---|
| 3,200,701 | 8/1965 | White | 340/146.3 E |
| 3,292,149 | 12/1966 | Bourne | 340/146.3 E |
| 3,482,498 | 12/1969 | Becker | 340/146.3 E |
| 3,648,240 | 3/1972 | Jacoby et al. | 340/146.3 E |
| 3,743,421 | 7/1973 | Maloney | 250/550 |

OTHER PUBLICATIONS
Claassen et al., "Fingertip Orienting and Ridge Viewing Apparatus," IBM Tech. Disclosure Bulletin, vol. 8, No. 3, 8-1965, pp. 435-436.

*Primary Examiner*—Leo H. Boudreau
*Attorney, Agent, or Firm*—Howard P. Terry

[57] ABSTRACT

A fingerprint optical sensor terminal is provided for use in the real time recording of an impression of a fingerprint pattern, the human finger being placed for the purpose at an input window surface of the sensor terminal. The sensor terminal provides precise angular and positional alignment of the finger and affords the immediate recognition of the presence of a finger that would produce a poor impression, permitting prompt corrective action by the operator. The sensor terminal also permits the making of an impression of a wide area of the finger, thus providing increased discrimination and accuracy of print identification with increased economy.

8 Claims, 6 Drawing Figures

REAL TIME FINGERPRINT RECORDING TERMINAL

BACKGROUND OF THE INVENTION

1. Field of the Invention

The invention relates generally to efficient and reliable sensor terminal means for generation of fingerprint impressions or related patterns at an optical input window of a data processor and more particularly relates to such apparatus whereby the satisfactory or non-satisfactory character of the impression is visually and rapidly assessed prior to manipulation by a data processor for comparison and recognition purposes.

CROSS REFERENCE TO RELATED CASES

The following application employs the same drawings and description of the preferred embodiments as are used in the present application, claiming different features of the apparatus disclosed therein: Ser. No. 502,116 for a "Real Time Fingerprint Recording Terminal," filed Aug. 30, 1974 in the names of Donald H. McMahon and Colin G. Whitney and assigned to Sperry Rand Corporation. 2. Description of the Prior Art Prior art apparatus for generation of fingerprint impressions has been difficult and time consuming to use with data processing systems, such apparatus generally lacking means to insure that an adequate print impression has been made before it is optically scanned and placed in the data processor in the form, for example, of binary data. Moreover, neither the fullness of the print nor its position on the input window surface are exactly known. A consequence is a time delay in the injection of the data into the processor which data may, in any event, prove to be inadequate. Thus, the average time required for correlation and actual recogition of the input fingerprint is needlessly increased. Further lost time entails the fact that the operator will not generally know why the print impression is not adequate and will therefore not realize what corrective step is to be taken to remedy the situation. In addition, many prior art fingerprint impression devices depend upon rolling the finger in order to produce the impression, a procedure that may seriously distort the impression, rendering it useless for automatic comparison purposes.

SUMMARY OF THE INVENTION

The present invention is an optical fingerprint sensor terminal for use in the real time recording of an image of a fingerprint pattern, the human finger being placed for the purpose at an input window surface of the sensor terminal. The sensor terminal affords the immediate visual recognition of the presence of a finger that would produce a poor impression, permitting accurate and prompt corrective action to be taken before the data is processed. The sensor terminal also permits making an impression of a wide area of the finger being examined, thus providing increased data for improved discimination and rapid, accurate identification of fingerprints with increased economy. The sensor terminal also provides a means for repositioning the finger with high accuracy in angular orientation and moderate accuracy in translational positioning. Improved positioning accuracy reduces the time or hardware cost required to carry out the subsequent comparision of fingerprint pattern data. Improved and more efficient use of a central data processor may be obtained, even with use of fewer input sensors.

DESCRIPTION OF THE PREFERRED EMBODIMENTS

Figure 1:
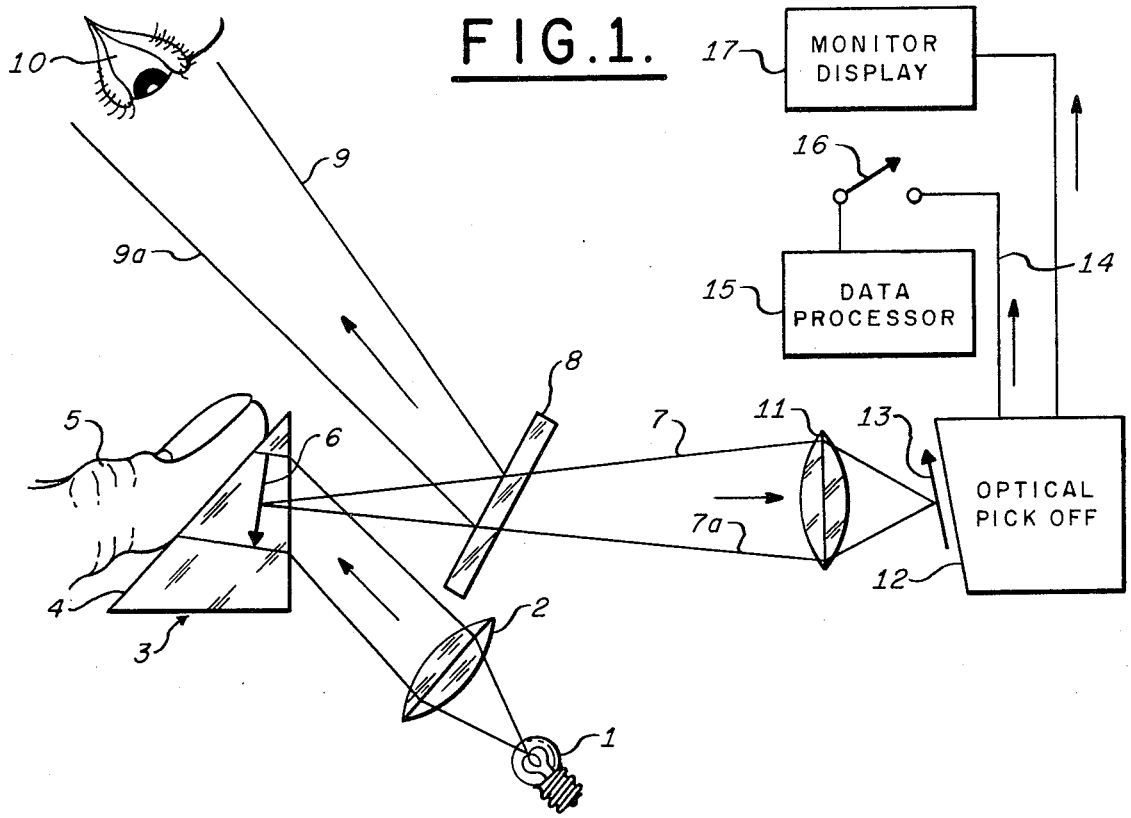
FIG. 1 is an elevational view of one embodiment of the invention, illustrating its optical components and their relation to data processor equipment.

The invention presented in FIG. 1 is a novel optical sensor terminal adapted for use, for example, in the real time recording of a binary or other image of a fingerprint pattern, the human finger being placed for the purpose at an input window surface of the optical sensor terminal. For providing a clear understanding of the invention, it will be advantageous to discuss prior art fingerprint input window surfaces in further detail and certain aspects of them in relation to operation in real time.

There are two general kinds of input window surfaces that have been used in the prior art for real time recording of fingerprint impressions. In one case, the finger to be examined is placed in contact with an internally illuminated surface of a transparent glass prism, light being scattered from those regions of the prism surfaces that are in direct contact with the tops of fingerprint ridges. Either the non-scattered, reflected light or the scattered light may then be used, for example, by known auxiliary apparatus to generate fingerprint information for storage, comparison, or other data processor use. Such prism apparatus is of the general class described by D. H. McMahon in the U.S. Pat. No. 3,771,124 for a "Coherent Optical Processor Fingerprint Identification Apparatus" or by D. H. McMahon in the U.S. Pat. No. 3,771,129 for an "Optical Processor Fingerprint Identification Apparatus." Both patents issued Nov. 6, 1973 and are assignd to Sperry Rand Corporation. In another prior art approach to the problem, a grease impression is produced on clean transparent tape by direct contact with the finger and the grease impression is then read by auxiliary equipment which may include coherent or non-coherent optical apparatus.

Successful use may be made of the transparent tape fingerprint sensor where the operator is given adequate training, such training including learning to judge how hard to press the finger being examined against the tape in order to obtain a clear, unsmeared impression containing an optimum amount of grease. The amount of grease retained on the tape surface is, of course, also a function of how dry the finger happened to be at the time the contact was made. For example, a freshly washed hand will generally not yield a satisfactory impression. Wiping a finger across the forehead will normally supply an additional amount of grease which may be sufficient depending upon the particular optical system being used by the sensor. In some situations, supplementary amounts are required of a grease even more viscous than the naturally occurring body grease.

In general, the problem of assuring the presence of the correct amount of grease on the finger to be examined for generating a useful impression confronts both the novice user of the fingerprint recording terminals as well as the more seasoned expert. While an experienced user of prior art equipment can produce a satisfactory grease impression most of the time, a novice may experience great difficulty in doing so.

The prism apparatus involves a generally easier to use window input surface, but it is still not possible to guarantee that good fingerprint impressions will always be produced. As in the instance of the transparent tape input system, excessively clean or dry hands may not produce an acceptable impression. Moreover, neither the fullness of the print nor the position of the print on the input window surface are exactly known to the operator at the time the impression is made, and neither may be adequate a sufficient amount of measured data for the data processor.

In the prior art systems, the operator can not readily verify that adequate input data is available in the form of a proper impression before the data is scanned and transferred to the associated computer system for processing. In the usual computer apparatus, the derived data is condensed, adjusted to eliminate the effects of translation and angular misorientation, and is then compared with stored digital data to establish correlation of the input data with a similar and previously recorded set of digital data. A natural consequence is that a time delay of several seconds is incurred each time that inadequate data is supplied at the input window surface; thus the average time required for actual recognition of the input fingerprint is increased. A further factor of major importance is that the operator will not, in general, know why the fingerprint impression is inadequate. Consequently, the operator will not know the proper corrective step to take to avoid repetition of the same failure. The total effect is a reduced accuracy of identification a reduced flow rate of candidates for fingerprint examination through the system, and a general loss of confidence in the utility of the fingerprint sensor terminal itself.

According to the invention, there is provided novel means for the significant reduction or elimination of the time lost in use of prior art fingerprint sensor apparatus. A primary object is to eliminate poor recognition accuracy due to the generation of inadequate fingerprint impressions, thereby significantly reducing the subsequent delays in computer processing of the fingerprint data, thus considerably decreasing the average time required for the reliable recognition of fingerprints.

One feature of the present invention provides a visual display of the figerprint impression instantaneously as it is generated on the input window surface. The novel feature permits the operator, in advance of the data processing steps to verify that a fully adequate fingerprint impression worthy of processing is being offered. Accordingly, in the presence of an inadequate impression, the operator may take the appropriate corrective steps for producing an adequate fingerprint. The fullness of the fingerprint impression may be observed visually and the adequacy of the print location may be assessed. The invention thus provides a real time fingerprint terminal which yields a visual display of the fingerprint impression immediately as it is being produced and therefore provides the desirable possibility of prompt corrective action by the operator.

In the invention as represented in FIG. 1, the fingerprint is illuminated from below by light from an approximate point source provided by lamp 1, the rays of light being made generally parallel by lens 2 and then refracted upon entering the 90° isosceles prism 3. The finger 5 whose print is to be examined is caused to contact the input window surface 4 of prism 3 and the fingerprint is therefore illuminated by the refracted light. Substantially only light scattered from portions (normally ridge tops) of the fingerprint in actual contact with the input face 4 of prism 3 forms an effective object at 6 at the focal point of imaging lens 11. Thus, the rays 7, 7a from a representative point on the effective object 6 are focused at a point in the image plane of lens 11. In the same manner, all points of the effective objects 6 are similarly focused to form image 13 at the input plane of optical pick up 12 for examination and correlation by a conventional data processor 15.

Interposed between prism 3 and the imaging lens 11 is a tilted half-silvered mirror 8 which permits the observer at 10 to look directly at the effective object 6. The scattered light reaching the observer's eye provides a bright, high contrast, substantially life-sized image of the fingerprint pattern as it is instantaneously produced when finger 5 is placed in contact with the input window surface 4. Alternatively, the observer 10 may view the display of a conventional raster scanning monitor display 17 presenting the scanned image detected by optical pick up 12, which may be a conventional vidicon type of image detector or camera. In this manner, the operator may determine visually if the print is adequate and why it is not if it is not. He may then translate data from optical pick up 12 via leads 14 to data processor 15 by closing switch 16 only when a desirable print impression is available.

Extensive tests of the FIG. 1 embodiment of the invention have demonstrated its general feasibility and utility for sampling fingerprint ridge orientation in the high activity area of the fingerprint pattern. By high activity regions is meant those normally central areas of the print pattern where the changes in angle between neighboring sample measurement points is relatively large; the converse characterizes low activity regions normally not central with respect to the print. A beneficial aspect of the embodiment of the invention shown in FIGS. 2 and 3 derives from the fact that such useful discriminatory information can, in fact, be derived from the outer, low activity portions of fingerprint patterns. It is also found that such information may be derived in spite of frequent naturally occurring distortion of the finger when the printing contact is made.

While the total area of the fingerprint impression may be substantially increased by rolling the finger across a flat surface, such as the window surface 4 of prism 3 in FIG. 1, the rolling motion often produces serious distortion of the impression which can not generally be reproduced from one fingerprint impression to the next. Thus, the natural flexibility and elasticity of the human finger tends to degrade the accuracy, reliability, and repeatability of the fingerprint recognition process.

According to the second embodiment of the invention, a fingerprint impression is produced that corresponds to a substantially greater area of the finger than that produced by a flat, non-rolled impression without using the rolling motion which causes pressure distortion of the impression. This embodiment also overcomes difficulties characterizing prior art attempts to simulate the making of a rolled fingerprint impression but without actual rolling of the finger to be examined. In one such prior art device, it is attempted to roll an image receiving card about the finger to provide an inked impression, but distortion of the finger being examined is not avoided. More complex and expensive arrangements have been proposed using an array of optical fibers.

Figure 2:
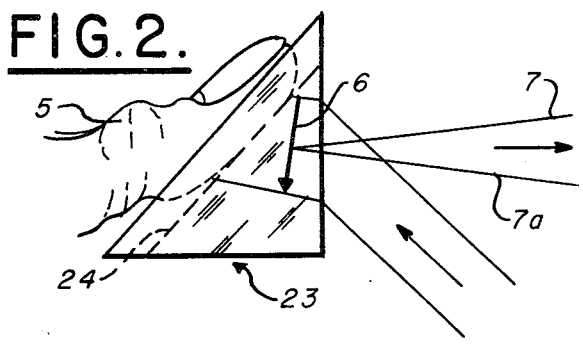
FIG. 2 is an elevation view of a novel alternative form of an optical element used in FIG. 1.
Figure 3:
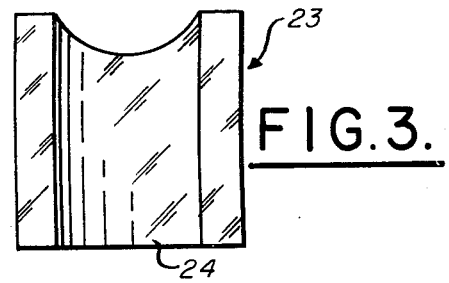
FIG. 3 is a front elevation view of the optical prism of FIG. 2.

In the apparatus of FIGS. 2 and 3, a prism 23 with a curved re-entrant cylindrical window surface 24 is employed. The form of surface 24 may be a sector of a circular cylinder having a diameter slightly greater than the finger to be examined. A series of such prisms may be supplied to accommodate corresponding ranges of finger diameters. Again, only light scattered from the now greater portion of the finger in contact with the curved window 24 of the prism reaches an imaging lens corresponding to lens 11 of FIG. 1 and is imaged on the optical pick up input plane 13. The optical pick up or vidicon device 12 again scans the finger-print image in a conventional manner and supplies a stream of data via leads 14 sufficient for data processor 15 to reconstruct the essential details of the fingerprint pattern. The cylindrical channel of the prism 23 also functions as a finger positioning device. In the desired mode of operation, the finger 5 is placed in alignment with the cylindrical channel in contact with the bottom of the channel and in contact with a stop surface placed at the inner end of the channel. The channel therefore serves as a positioning surface which permits sufficiently accurate registration of the fingerprint pattern that the burden of subsequent processing steps is greatly reduced.

Figure 4:
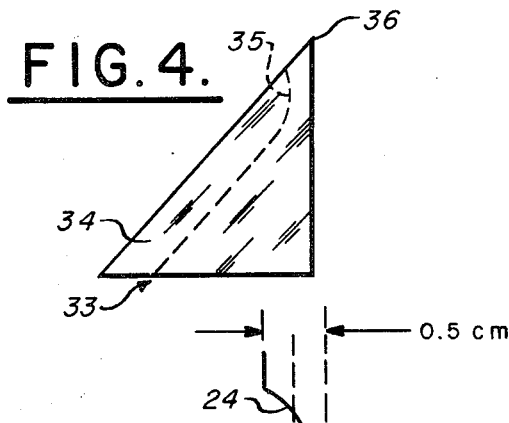
FIGS. 4 and 5 are corresponding views of an alternative form of the prism of FIGS. 2 and 3.
Figure 5:
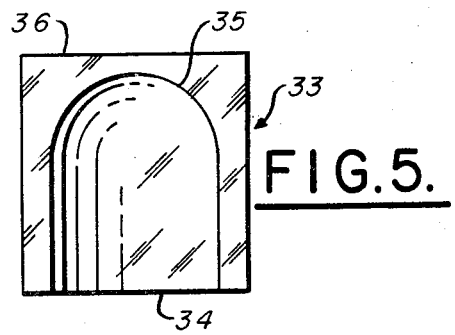

In the additional embodiment of FIGS. 4 and 5, the prism 33 is provided with a curved concave surface 34 similar to surface 24 of FIGS. 2 and 3, but surface 34 does not continue essentially to the upper apex 36 of the prism as it does in FIGS. 2 and 3. Instead, the surface 34 is terminated by a smoothly connected surface 35 which may approximate a sector of a spherical surface. In this manner, the pattern on the tip of a finger to be examined may be printed, as well as the side portions of the finger that may be imprinted on the window surface 24 of prism 23 of FIG. 2.

Figure 6:
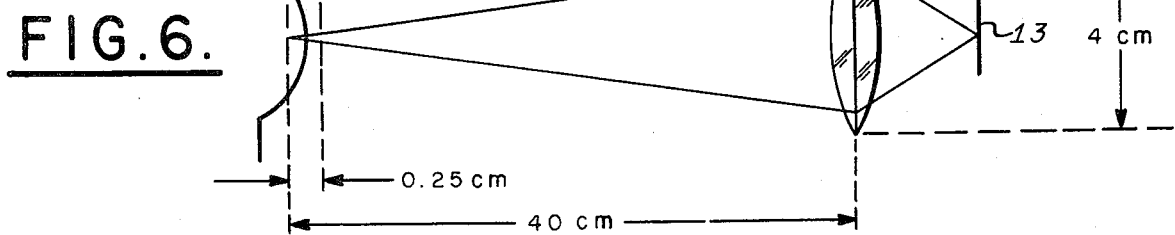
FIG. 6 is an explanatory plan view of portions of FIG. 1.

As is seen in FIG. 6, the aperture of the imaging lens 11 to be used with any of the trio of prisms is chosen to be sufficiently small and the distance between lens 11 and the prism 3 or 23 is chosen to be sufficiently large that the curved field of the fingerprint impression is in acceptably good focus at location 13 which is occupied, for example, by the target electrode of the vidicon device. The large distance between the prism and the lens is also beneficial as it minimizes magnification distortion over the angular extent of the fingerprint impression caused by the varying object-image ratio. By way of example, assume that the depth of the curved portion of the prism window 24 in contact with the finger is about 0.5 centimeters and that the prism-to-lens distance is about 40 centimeters. For a typical fingerprint in which there are twenty ridge lines per centimeter, the aperture for lens 11 would not be greater than about 4 centimeters for good focused images to be seen.

It is seen that the novel fingerprint terminal permits a significant increase in the flow of persons whose fingerprints are to be examined. In a multiple terminal complex using a single central data processor, the number of fingerprint sensors required to handle a given number of people may be reduced, thereby decreasing the system installation and operation cost. Moreover, the presence of a finger which would otherwise tend to produce a poor fingerprint impression may be at once visually observed, and a quick selection may be made of the one best of ten print impressions, for example. Likewise, if the skin of the finger to be examined has been cut or otherwise damaged or is scarred, the physical damage can at once be visually noted. Corrective action, such as entering data from a different finger, can at once be taken with consequent saving in time. The invention additionally increases accuracy and therefore saves operating time by virtue of the fact that it provides wider fingerprint impressions without disadvantageous rolling and distortion of the finger, thus providing increased discrimination and accuracy of print identification.

While the invention has been described in its preferred embodiments, it is to be understood that the words which have been used are words of description rather than of limitation and that changes within the purview of the appended claims may be made without departure from the true scope and spirit of the invention in its broader aspects.

I claim:

1. Apparatus for forming an image of a fingerprint pattern for comparison with a stored pattern comprising:
    transparent right triangular prism means characterized by first and second opposed sides, first and second intersecting sides forming a common first edge, and a major side forming common second and third edges with said respective first and second intersecting sides,
    said major side having a concave portion therewithin adapted for contact by the ridges of a finger,
    light source means for forming a substantially parallel light beam having a first optical axis for incidence upon said first intersecting side whereby said light beam is refracted to illuminate said ridges at said concave portion for forming a first image of said ridges within said prism adjacent said first intersecting side, and
    image forming lens means on a second optical axis for forming a second image in response to said first image.

2. Apparatus as described in claim 1 wherein said concave portion comprises a section of a cylinder.

3. Apparatus as described in claim 2 wherein said section of a cylinder is substantially a circular section of a cylinder.

4. Apparatus as described in claim 3 wherein said cylinder has an axis substantially perpendicular to said first common edge.

5. Apparatus as described in claim 3 wherein said section of a cylinder is so dimensioned as to constrain the lateral position of a finger and is further contoured to determine the longitudinal position of the finger.

6. Apparatus as described in claim 4 further including:
    image scanning means for scanning said second image,
    and
    monitor display means for providing an enlarged display of said second image in response to said image scanning means.

7. Apparatus as described in claim 4 further including:

image scanning means for scanning said second image, and data processor means selectably operable at the will of the operator for comparison of said second image with a stored pattern.

8. Apparatus for forming an image of a fingerprint pattern comprising:

transparent triangular prism means characterized by first and second opposed sides, first and second intersecting sides forming a common first edge, and a major side forming common second and third edges with said respective first and second intersecting sides, said major side having a concave portion therewithin adapted for contact by the ridges of a finger, said concave portion having the form of a circular section of a cylinder whose effective axis is substantially perpendicular to said first common edge, light source means for passing a light beam through said prism for incidence upon said ridges at said concave portion for forming a first image of said ridges within said prism, said concave portion being contoured at one end to determine the longitudinal position of the finger whereby said first image integrally includes substantial portions of the ridges of the tip of the finger, and means for utilizing said first image.

\* \* \* \* \*